(12) United States Patent
Goff

(10) Patent No.: US 7,618,252 B1
(45) Date of Patent: Nov. 17, 2009

(54) BALLOON PLEATING MECHANISM

(76) Inventor: Ed Goff, 4718 N. 33rd St., Phoenix, AZ (US) 85018

( * ) Notice: Subject to any disclaimer, the term of this patent is extended or adjusted under 35 U.S.C. 154(b) by 44 days.

(21) Appl. No.: 11/877,532

(22) Filed: Oct. 23, 2007

Related U.S. Application Data

(60) Provisional application No. 60/853,885, filed on Oct. 24, 2006.

(51) Int. Cl.
  *B29C 53/08* (2006.01)
(52) U.S. Cl. .................. 425/392; 425/397; 425/402; 72/402; 29/237
(58) Field of Classification Search ............... 425/392, 425/393, 402–403, 397; 72/402; 29/237
  See application file for complete search history.

(56) References Cited

U.S. PATENT DOCUMENTS 1,889,795 A * 12/1932 Smith et al. ............... 29/516

6,360,577 B2 * 3/2002 Austin ........................ 72/402
6,988,881 B2 * 1/2006 Motsenbocker et al. ..... 425/392

* cited by examiner

*Primary Examiner*—Yogendra Gupta
*Assistant Examiner*—Thu Khanh T Nguyen
(74) *Attorney, Agent, or Firm*—Parson & Goltry; Robert A. Parsons; Michael W. Goltry

(57) ABSTRACT

Balloon pleating mechanism includes a plurality of pleating dies, each having a first planar guiding surface, a second planar guiding surface, a bearing surface, a first working surface, and a second working surface. The plurality of pleating dies are arranged in a generally circular orientation with the first planar guiding surface of each die being in sliding contact with the second planar guiding surface of an adjacent die and the first working surface and the second working surface of each die of the plurality of dies cooperating to define a central cavity. The plurality of pleating dies is further arranged for relative radial movement between an open position and a closed position. A driving mechanism is coupled to each die and designed to move the plurality of dies between the open position and the closed position.

21 Claims, 5 Drawing Sheets

BALLOON PLEATING MECHANISM

CROSS-REFERENCE TO RELATED APPLICATION

This application claims the benefit of U.S. Provisional Application No. 60/853,885, filed 24 Oct. 2006.

FIELD OF THE INVENTION

This invention relates to medical device manufacturing equipment.

More particularly, the present invention relates to medical balloon catheter pleating devices.

BACKGROUND

As part of the manufacture of medical balloon catheters, balloons must be wrapped or folded tightly around the catheter shaft. Typically, balloons are formed into some number (usually 2 to 6) of equal "wings" that are wrapped spirally around the central shaft. Precise wrapping decreases the diameter of the overall catheter balloon, which is important to the catheter's ability to be delivered to the desired site.

The process of wrapping or folding a balloon typically consists of two main steps: a pleating step, in which the wings are formed, and a compression or wrapping step in which the wings are pressed tightly against the catheter shaft and formed permanently into the wrapped shape, usually by both heating and pressure. For both of these steps, the prior art includes several mechanisms and methods. The present invention addresses the pleating step.

One mechanism for pleating a balloon is the "Balloon Folding Fixture" sold by Interface Associates. The mechanism comprises several dies (the number of dies being equal to the desired number of wings) shaped so that, when the dies are moved in unison radially inward toward a centrally-placed, inflated balloon, the balloon is formed into the desired pleated shape. A central cavity is formed when all the dies are moved inward, the cavity having, in cross section, a round shape at the center to accommodate the catheter central shaft, and thin, curved gaps for the wings spiraling outward from the center. Each die is guided by a commercially-available linear guide and driven by a separate stepper motor, with all the linear guides and stepper motors mounted to a common base plate. A shortcoming of this mechanism is that, because of the many parts, attachments, and motor controls that influence the shape and size of the central cavity, the cavity is not sufficiently accurate to repeatably and precisely form the pleated balloon without damage to the balloon.

Another mechanism for pleating a balloon is one used in the "FFS" equipment sold by Machine Solutions Inc., and described in U.S. Pat. No. 6,988,881. The mechanism comprises several dies (the number of dies being equal to the desired number of wings) shaped so that, when the working tips of the dies are moved in unison inward toward a centrally-placed, inflated balloon, the balloon is formed into the desired pleated shape. A central cavity is formed when all the dies are moved inward, the cavity having, in cross section, a round shape at the center to accommodate the catheter central shaft, and thin, curved gaps for the wings spiraling outward from the center. The dies are pivotally coupled to a common base member or hub, and driven in unison by a rotatable drive hub. A shortcoming of this mechanism is that, because of the many parts and attachments that influence the shape and size of the central cavity, the cavity is not sufficiently accurate to repeatably and precisely form the pleated balloon without damage to the balloon.

Another mechanism for pleating a balloon is described in U.S. Pat. No. 6,623,689. In this mechanism, the balloon is pulled axially through a cavity of varying cross section to first form the pleats, then radially compress the balloon. A shortcoming of this method is that the balloon slidingly engages the tooling, introducing a potential for damage to the balloon by scratching or abrasion.

Another mechanism for pleating a balloon is described in U.S. Pat. No. 5,783,227. In this mechanism, two die halves are moved inward toward a centrally-placed, inflated balloon, forming the balloon into a two-pleated shape. A central cavity is formed when all the dies are moved inward, the cavity having, in cross section, a round shape at the center to accommodate the catheter central shaft, and thin, radially-outward gaps for the wings. A shortcoming of this mechanism is that only two wings can be formed in the balloon.

It would be highly advantageous, therefore, to remedy the foregoing and other deficiencies inherent in the prior art.

Accordingly, it is an object of the present invention to provide a new and improved balloon pleating mechanism.

Another object of the invention is to provide a new and improved balloon pleating mechanism for pleating balloons for use in devices such as stents, catheters, and the like in the medical industry.

Another object of the invention is to provide a new and improved balloon pleating mechanism that accurately and repeatably pleats balloons used in the medical industry without damaging or weakening the balloons.

SUMMARY OF THE INVENTION

Briefly, to achieve the desired objects of the present invention in accordance with a preferred embodiment thereof provided is a balloon pleating mechanism including a plurality of pleating dies each having a first planar guiding surface, a second planar guiding surface, a bearing surface, a first working surface, and a second working surface. The plurality of pleating dies are arranged in a generally circular orientation with the first planar guiding surface of each die being in sliding contact with the second planar guiding surface of an adjacent die and the first working surface and the second working surface of each die of the plurality of dies cooperating to define a central cavity. The plurality of pleating dies is further arranged for relative radial movement between an open position and a closed position. The planar guiding surfaces constrain the motion of the dies so that the dies move in unison. A driving mechanism is coupled to each die and designed to move the plurality of dies between the open position and the closed position.

The desired objects of the present invention are further achieved in accordance with a more specific embodiment of the present invention including a plurality of pleating dies each having a first planar guiding surface, a second planar guiding surface, a bearing surface, a first working surface, and a second working surface. The plurality of pleating dies are arranged in a generally circular orientation with the first planar guiding surface of each die being in sliding contact with the second planar guiding surface of an adjacent die and the first working surfaces and the second working surfaces of the plurality of dies cooperating to define a central cavity. The plurality of pleating dies is further arranged for relative radial movement between an open position and a closed position. The planar guiding surfaces constrain the motion of the dies so that the dies move in unison. A plurality of bearing apparatus are positioned to suspend each die and to hold the plurality of dies together in close sliding contact, one bearing apparatus of the plurality of bearing apparatus being associated one each with each die of the plurality of dies. In a preferred embodiment each bearing apparatus includes a roller bearing positioned in engagement with the bearing surface of the associated die of the plurality of dies. The roller bearing of each bearing apparatus is mounted on a post having a fixed position with relation to the plurality of dies (e.g. the post is fixedly mounted on a housing or base). A driving mechanism is coupled to each die of the plurality of dies and designed to move the plurality of dies between the open position and the closed position.

BRIEF DESCRIPTION OF THE DRAWINGS

Specific objects and advantages of the invention will become readily apparent to those skilled in the art from the following detailed description of a preferred embodiment thereof, taken in conjunction with the drawings in which.

DETAILED DESCRIPTION OF A PREFERRED EMBODIMENT

Figure 1:
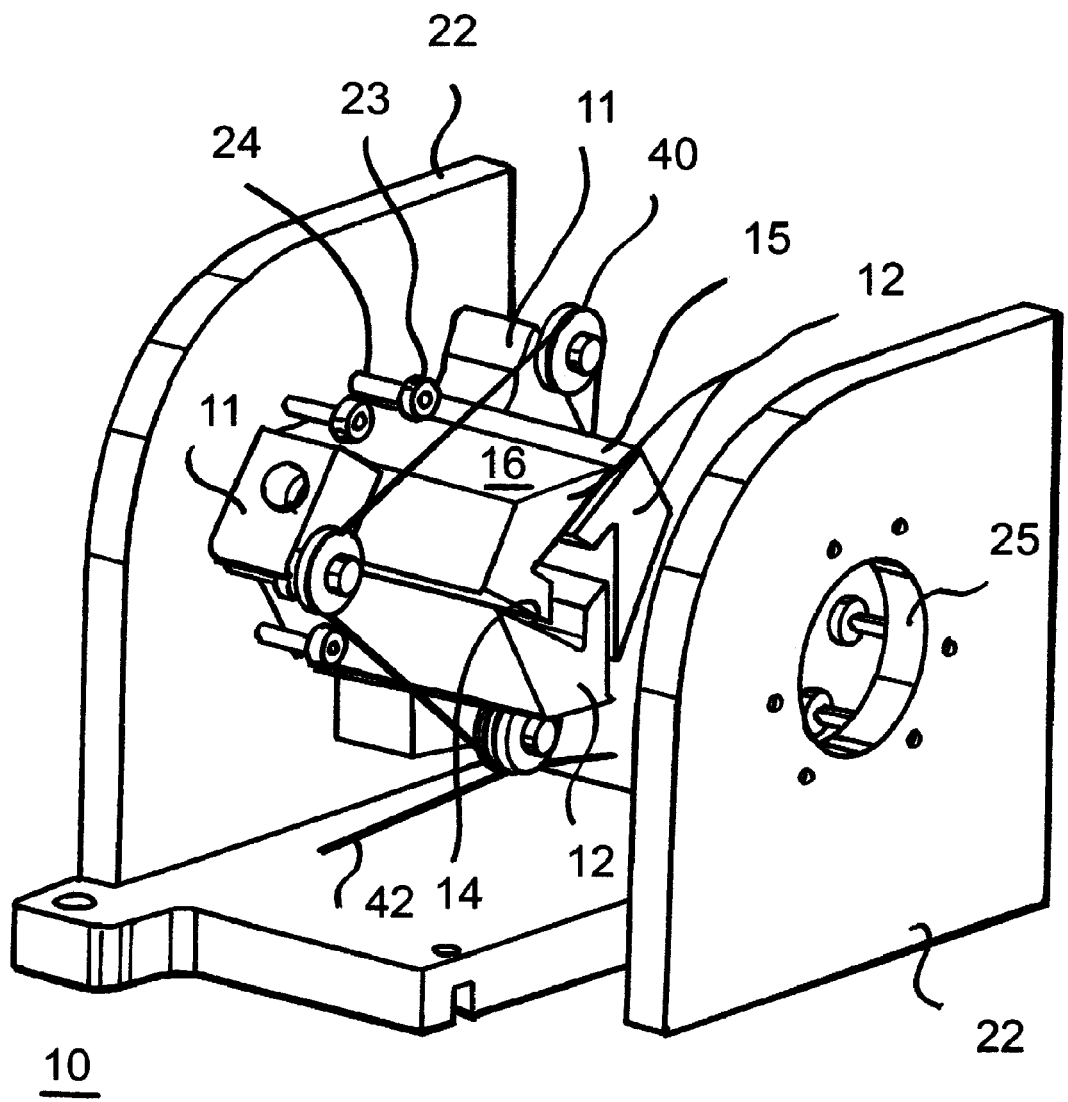
FIG. 1 is a simplified perspective view of a balloon pleating mechanism according to the present invention.
Figure 2:
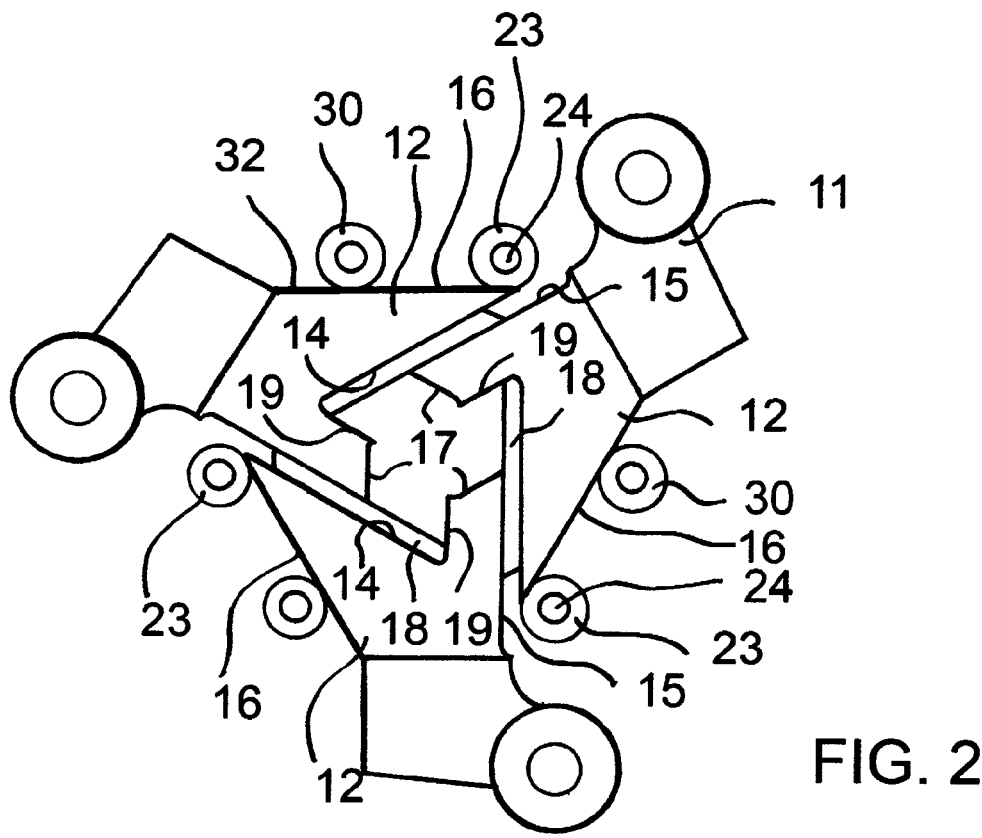
FIG. 2 is a simplified view illustrating the pleating dies in an open position.

Turning now to the drawings in which like reference characters indicate corresponding elements throughout the several views, attention is first directed to FIG. 1 which illustrates a balloon catheter pleating mechanism generally designated 10. Pleating mechanism 10 includes a plurality of dies 12 (in this embodiment three) shaped so that, when dies 12 are moved in unison radially inward from an open position (illustrated in FIG. 2) toward a centrally-placed, inflated balloon (not shown), the balloon is formed into the desired pleated shape. The number of dies used can be any desired number, generally from three to nine, with the number of dies used being equal to the desired number of wings in the pleated balloon.

Each die 12 is an elongated block of material, such as stainless steel, hard plastic, etc., extending substantially between spaced apart end plates 22 of pleating mechanism 10. The dies 12 are arranged generally in a circle with a driving mechanism 11 positioned on a generally circumferentially oriented outer surface. Each die 12 includes a first planar guiding surface 14, a second planar guiding surface 15, a bearing surface 16, a first working surface 17, and a second working surface 19. The shape of each die 12 is irregular with, in the case of three pleats, surfaces 15 and 17 joining along an edge with an angle of approximately 60°, surfaces 14 and 16 joining along an edge with an angle of approximately 30°, and surfaces 14 and 19 joining along a channel or trough at an angle of approximately 60°. Surfaces 17 and 19 are positioned at approximately 120° to each other and the juncture is slightly arcuate for reasons that will become clear presently. The above angles are included only for purposes of explanation and it will be understood that these angles will vary substantially with, for example, changes in the number of dies or in the formation (thin, curved or straight) of gaps forming the wings.

Figure 3:
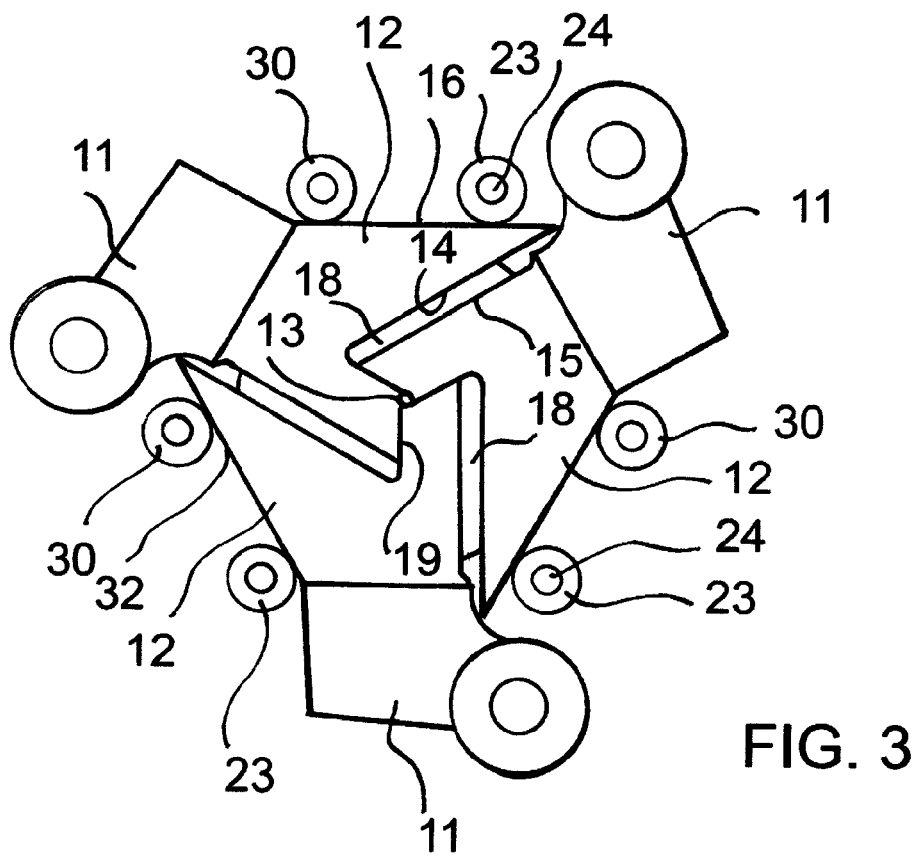
FIG. 3 is a simplified view illustrating the pleating dies in a closed position.

A central cavity 13 is formed when all of dies 12 are moved inward to a closed position (illustrated in FIG. 3), cavity 13 having, in cross section, a round shape at the center to accommodate the catheter central shaft, and thin, curved or straight gaps for the wings protruding outward from the center. In the preferred embodiment, the juncture of surfaces 17 and 19 is slightly arcuate to enhance the round or circular cross section of central cavity 13. Also, the thin, curved or straight gaps for the wings are defined by first working surface 17 of each die 12 in conjunction with second working surface 19 of an adjacent die 12. First planar guiding surface 14 of each die 12 is positioned parallel to and in "contact" with second planar guiding surface 15 of an adjacent die 12, which constrain dies 12 to move in a linear relationship relative to each other and to move in unison. Thus, dies 12 move in a very precise relationship relative to each other and, further, move precisely in unison. The inward or closing movement of dies 12 forms a very precise central cavity (cavity 13), without need for an attachment to any common base or hub. An advantage of this mechanism is that the movement of all of dies 12 in unison insures that balloons being pleated will not be frayed or damaged during the pleating operation.

Figure 5:
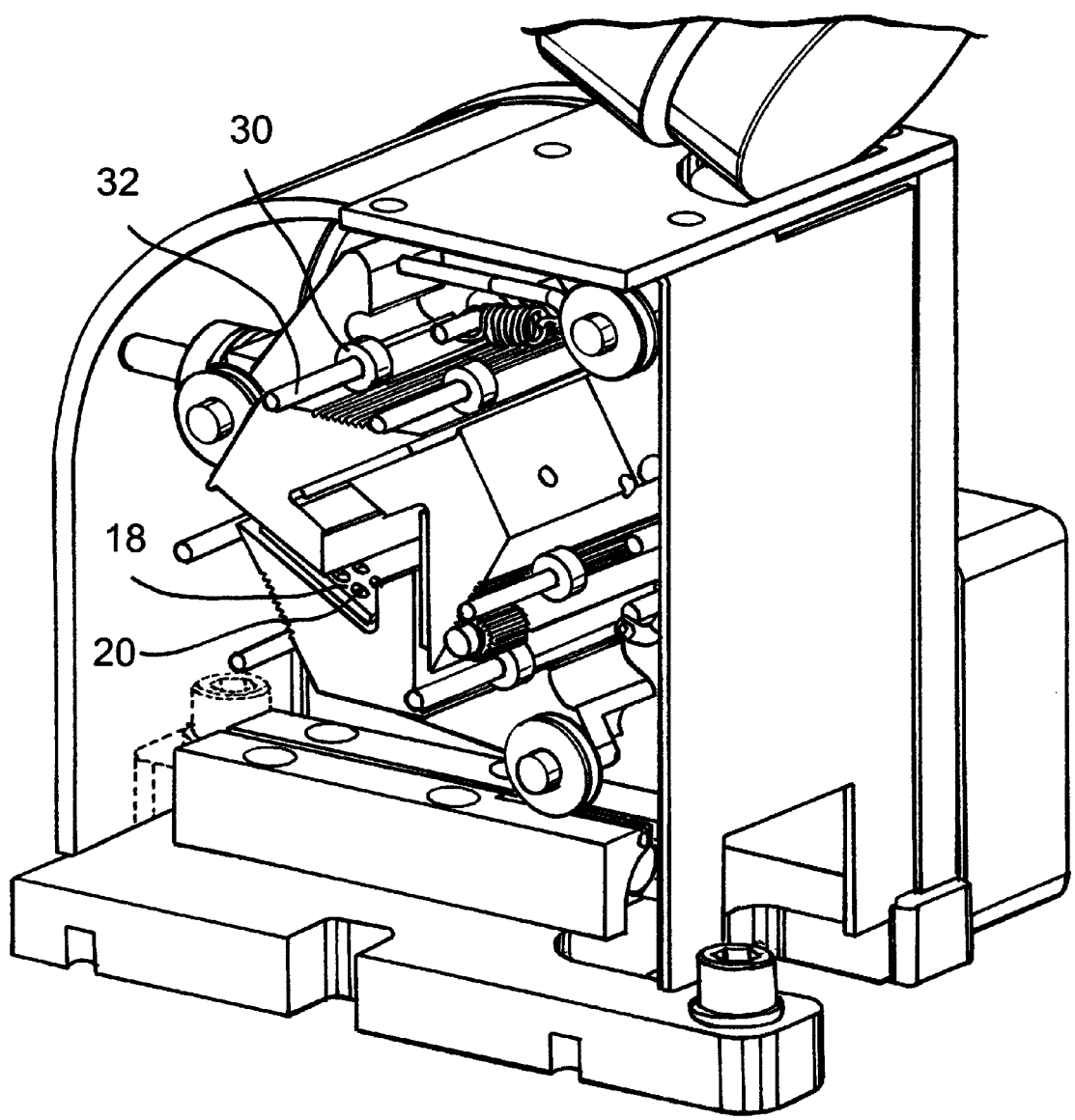
FIG. 5 is a side perspective view of the balloon pleating mechanism of FIG. 4 with a vertical bearing housing removed.

With additional reference to FIG. 5, in this embodiment, a ball cage 18 is mounted between first planar guiding surface 14 of each die 12 and second planar guiding surface 15 of each adjacent die 12. Ball cage 18 operates as bearing material or a bearing structure between first planar guiding surface 14 of a die 12 and second planar guiding surface 15 of an adjacent die 12. That is, a ball cage 18 is sandwiched between each adjacent set of planar guiding surfaces 14 and 15. Ball cage 18 is a flat piece of material, preferably Teflon that includes slots or openings for holding bearing balls 20 in a slightly protruding relation. The combination of ball bearings 20 and Teflon cage 18 permits smooth relative movement of adjacent dies 12. Bearing balls 20 are readily available, extremely accurately made and very inexpensive. Placing the combination of ball bearings 20 and Teflon cage 18 between adjacent dies 12 reduces the operating friction and wear of the mechanism. It should be understood that the term "contact" when referring to adjacent sets of planar guiding surfaces 14 and 15 includes embodiments in which the surfaces are in direct contact and surfaces between which some form of bearing material (e.g. ball cage 18, a simple Teflon surface, etc.) is included.

Referring again to FIG. 1, a plurality of bearing apparatus are included to mount the dies and to hold them in close sliding engagement. To this end the bearing apparatus of the present embodiment of mechanism 10 includes end plates 22 with roller bearings 23 mounted on posts 24 extending therefrom at each end of each die 12. A balloon introducing opening 25 in one end plate 22 is provided to allow the insertion of an inflated balloon into central cavity 13 and the removal of the balloon after pleating. In this embodiment three pairs of roller bearings 23 are used in conjunction with each end plate 22, one with each die 12 at each end, but it will be understood that more bearings could be used in special applications. A bearing 12 is positioned to engage a bearing surface 16 of each die 12 in a relative rolling relationship. Posts 24 and bearings 23 suspend each die 12 and hold dies 12 together so as to keep first planar guiding surfaces 14, ball cages 18, and second planar guiding surfaces 15 in close sliding engagement. In the preferred embodiment, posts 24 are slightly resilient and set slightly inwardly to allow bearings 23 to firmly contact surfaces 16 of dies 12 and to provide a bias that urges first planar guiding surfaces 14, ball cages 18, and second planar guiding surfaces 15 into a tight smoothly sliding relationship.

Figure 4:
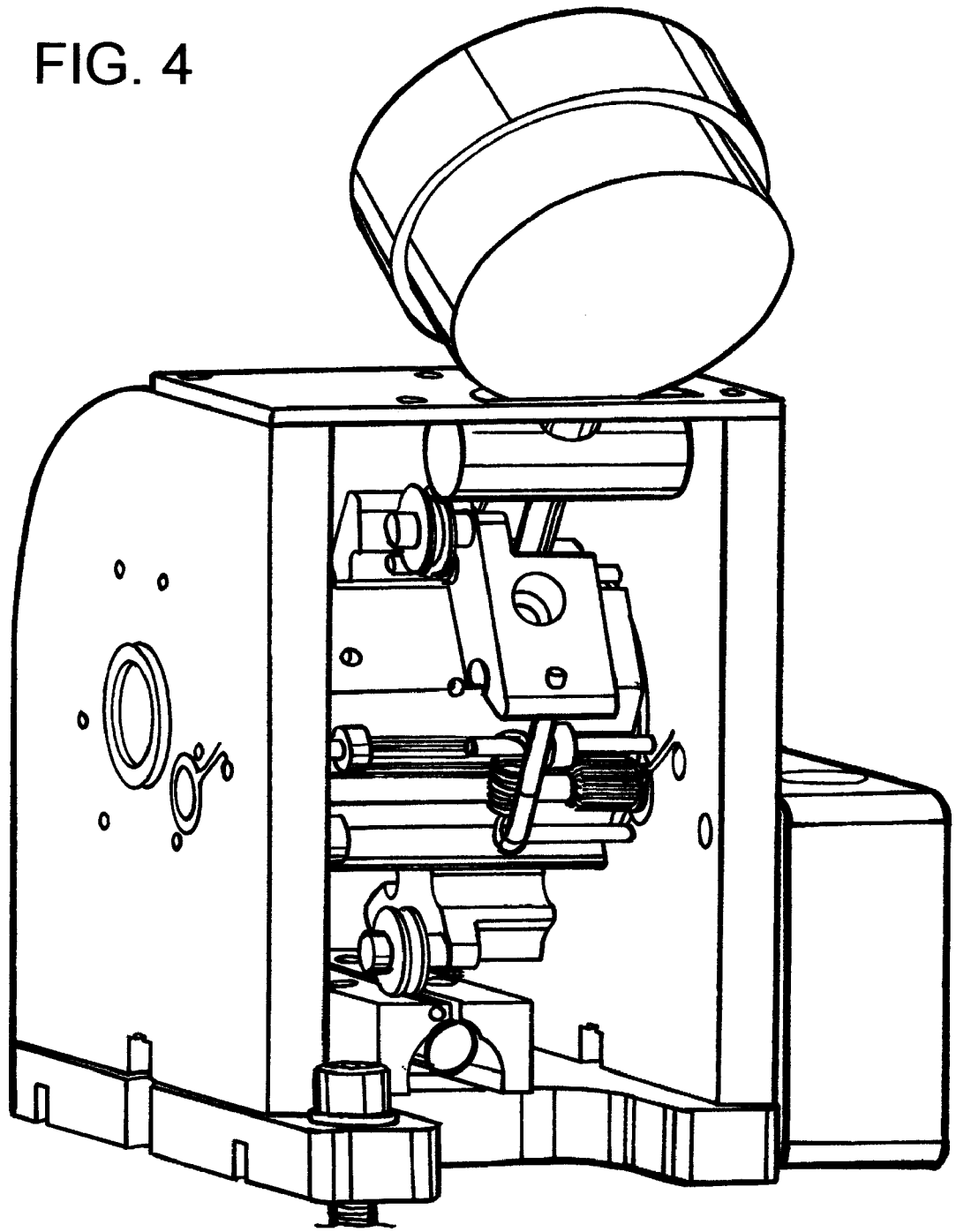
FIG. 4 is a detailed perspective view of the balloon pleating mechanism of FIG. 1.
Figure 6:
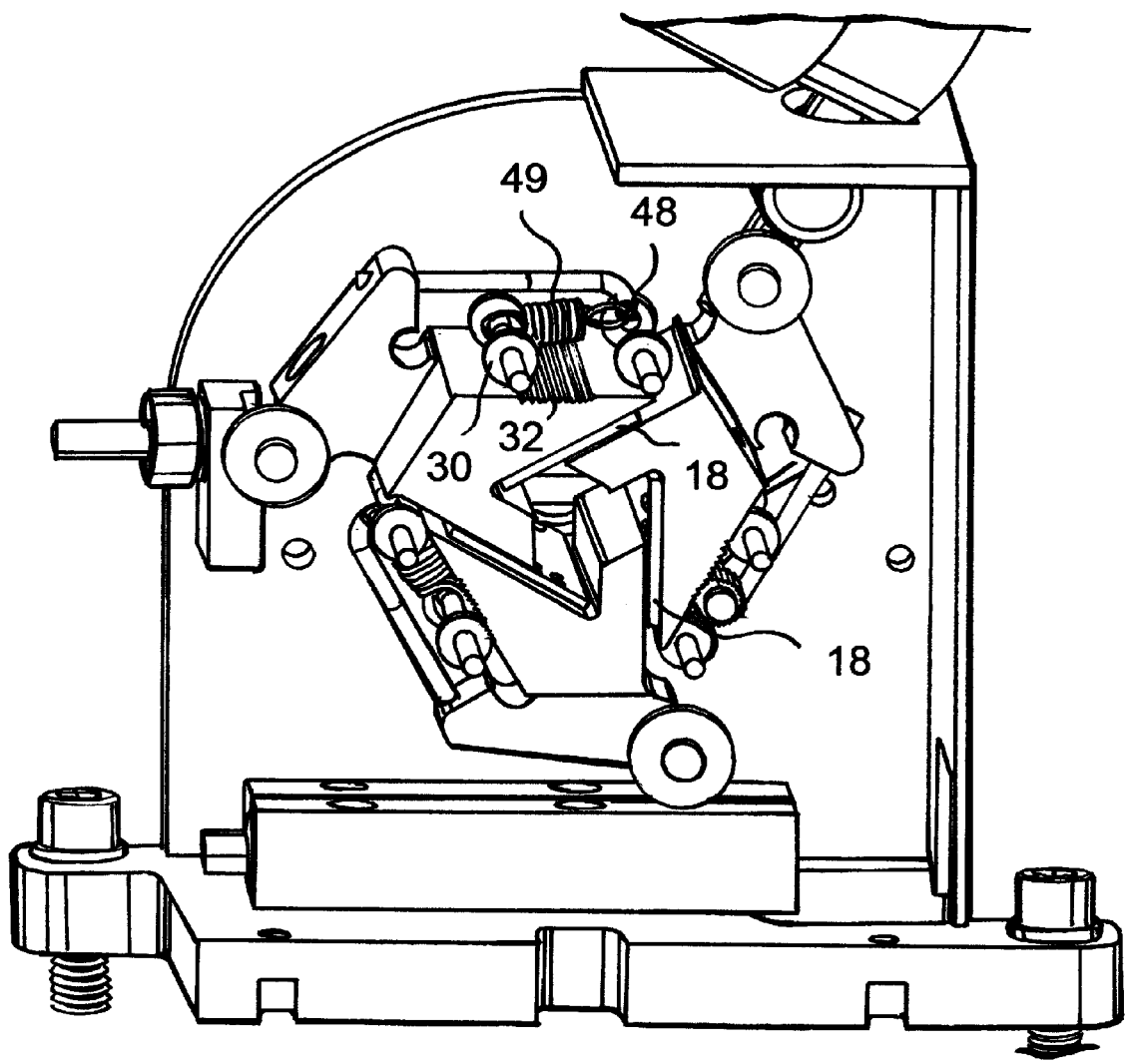
FIG. 6 is a side view of the mechanism of FIG. 5.

With additional reference to FIGS. 4 and 6, in order to keep working edges 17 of pleat dies 12 substantially parallel with the balloon to be pleated, a pinion gear 30 meshes with element gear teeth 32 of one or more dies 12 as the pleat mechanism is activated. As can be seen in FIGS. 5 and 6, element gear teeth 32 are positioned on bearing surface 16 of each die 12 so that the teeth extend longitudinally along surface 16 and are further positioned so that they do not interfere with the rolling engagement of bearing 23. Pinion gear 30 is supported on each end by a radial ball bearing that sits in a pinion bearing housing 35 (one illustrated in FIG. 4) which is a feature of the vertical end plates 22 that support the pleat head. To ensure that pinion gear 30 meshes with element gear teeth 32, pinion bearing housing 35 is connected to the rest of vertical end plate 22 solely by the pinion housing flexure which acts as a spring. The position of pinion bearing housing 35 places the pinion in slight interference with the element gear teeth and the meshing forces are determined by the thickness of the pinion housing flexure.

Still referring to FIG. 1, with additional reference to FIG. 6, pleating mechanism 10 also includes driving mechanism 11 positioned on a generally circumferentially oriented outer surface of each die 12. In this embodiment driving mechanism 11 includes a pulley 40 mounted to each die 12 with a cable 42 encircling all the pulleys 40 of dies 12 so that the application of tension to the cable produces a radially inward force causing the mechanism to close or move from the open to the closed position and pleat the balloon. One end of cable 42 is fixed and the other is attached to a plunger 45 (illustrated in FIG. 6), or other tension producing mechanism. The intermediate portion of cable 42 is wrapped around each of pulleys 40. When plunger 45 is pressed or actuated, cable 42 is put in tension and pleat dies 12 move radially inwardly towards each other, pleating the balloon.

In this embodiment, each die 12 has associated therewith a tension spring 47 stretched between a post 48 and one of the bearing posts 24. When plunger 45 is released or not pressed, cable 42 goes slack and tension springs 47 move dies 12 in unison away from each other, i.e. toward the open position. One or more return springs 47 are attached to one or more dies 12 and release of tension on cable 42 allows pleating mechanism 10 to open under the bias from spring or springs 47. While pulleys 40, cable 42 and plunger 45 are illustrated for their simplicity, movement repeatability, and reliability many actuation methods are possible, including human muscles, electric motors, or fluid-powered motors.

Thus, a new and improved balloon pleating mechanism has been disclosed for pleating balloons for use in devices such as stents, catheters, and the like in the medical industry. The new and improved balloon pleating mechanism is designed to accurately and repeatably pleat balloons used in the medical industry without damaging or weakening the balloons. In the pleating mechanism a plurality of dies are positioned in a substantially circular orientation and are guided by adjacent dies, constraining them to move in unison to pleat a balloon into a central portion with a plurality of outwardly extending wings. Because the dies move against each other and in unison the pleating operation is extremely accurate and repeatable. Also, the sliding engagement of the various parts prevents pinching, rubbing, or otherwise damaging the balloons during the operation.

Various changes and modifications to the embodiment herein chosen for purposes of illustration will readily occur to those skilled in the art. To the extent that such modifications and variations do not depart from the spirit of the invention, they are intended to be included within the scope thereof, which is assessed only by a fair interpretation of the following claims.

Having fully described the invention in such clear and concise terms as to enable those skilled in the art to understand and practice the same, the invention claimed is:

1. Balloon pleating mechanism comprising:
a plurality of pleating dies, each including a first planar guiding surface, a second planar guiding surface, a bearing surface, a first working surface, and a second working surface;
the plurality of pleating dies being arranged in a generally circular orientation with the first planar guiding surface of each die being in sliding contact with the second planar guiding surface of an adjacent die and the first working surface and the second working surface of each die of the plurality of dies cooperating to define a central cavity, the plurality of pleating dies being further arranged for relative radial movement between an open position and a closed position; and
a driving mechanism coupled to each die of the plurality of dies and designed to move the plurality of dies between the open position and the closed position.

2. Balloon pleating mechanism as claimed in claim 1 wherein the plurality of pleating dies is in a range of three to nine dies.

3. Balloon pleating mechanism as claimed in claim 1 further including bearing structure positioned between the first planar guiding surface of each die and the second planar guiding surface of an adjacent die.

4. Balloon pleating mechanism as claimed in claim 3 wherein the bearing structure includes a flat piece of bearing material.

5. Balloon pleating mechanism as claimed in claim 4 wherein flat piece of bearing material includes Teflon.

6. Balloon pleating mechanism as claimed in claim 4 wherein the bearing structure further includes a plurality of ball bearings mounted in the flat piece of bearing material.

7. Balloon pleating mechanism as claimed in claim 1 further including a plurality of bearing apparatus positioned to suspend each die and to hold the plurality of dies together in close sliding contact.

8. Balloon pleating mechanism as claimed in claim 7 wherein one bearing apparatus of the plurality of bearing apparatus is associated one each with each die of the plurality of dies, each bearing apparatus includes a roller bearing positioned in engagement with the bearing surface of the associated die of the plurality of dies.

9. Balloon pleating mechanism as claimed in claim 8 wherein the roller bearing of each bearing apparatus is mounted on a post having a fixed position with relation to the plurality of dies.

10. Balloon pleating mechanism as claimed in claim 9 wherein each of the posts is flexible and positioned to provide a radially inwardly directed bias on the plurality of dies.

11. Balloon pleating mechanism as claimed in claim 1 further including a pinion gear one each associated with each die of the plurality of dies, each pinion gear being positioned to mesh with element gear teeth mounted on the bearing surface of the associated die, the pinion gears keep the first and second working edges of the plurality of dies substantially parallel with a balloon to be pleated.

12. Balloon pleating mechanism as claimed in claim 1 wherein the driving mechanism includes a plurality of pulleys, one pulley of the plurality of pulleys affixed one each to one die of the plurality of dies.

13. Balloon pleating mechanism as claimed in claim 12 wherein the plurality of pulleys are coupled together with a common cable, the cable and pulleys being coupled to move in unison circumferentially so as to move the plurality of dies radially inwardly.

14. Balloon pleating mechanism comprising:
- a plurality of pleating dies each including a first planar guiding surface, a second planar guiding surface, a bearing surface, a first working surface, and a second working surface;
- the plurality of pleating dies being arranged in a generally circular orientation with the first planar guiding surface of each die being in sliding contact with the second planar guiding surface of an adjacent die and the first working surface and the second working surface of each die of the plurality of dies cooperating to define a central cavity, the plurality of pleating dies being further arranged for relative radial movement between an open position and a closed position;
- a plurality of bearing apparatus positioned to suspend each die and to hold the plurality of dies together in close sliding contact, one pair of bearing apparatus of the plurality of bearing apparatus being associated one each with each die of the plurality of dies, each bearing apparatus including a roller bearing positioned in engagement with the bearing surface of the associated die of the plurality of dies, the roller bearing of each bearing apparatus being mounted on a post having a fixed position with relation to the plurality of dies; and
- a driving mechanism coupled to each die of the plurality of dies and designed to move the plurality of dies between the open position and the closed position.

15. Balloon pleating mechanism as claimed in claim 14 further including a plurality of bearing structures, one each positioned between the first planar guiding surface of each die and the second planar guiding surface of an adjacent die.

16. Balloon pleating mechanism as claimed in claim 15 wherein each bearing structure of the plurality of bearing structures includes a flat piece of bearing material.

17. Balloon pleating mechanism as claimed in claim 16 wherein flat piece of bearing material includes Teflon.

18. Balloon pleating mechanism as claimed in claim 16 wherein each bearing structure of the plurality of bearing structures further includes a plurality of ball bearings mounted in the flat piece of bearing material.

19. Balloon pleating mechanism as claimed in claim 14 wherein the driving mechanism includes a plurality of pulleys, one pulley of the plurality of pulleys affixed one each to one die of the plurality of dies.

20. Balloon pleating mechanism as claimed in claim 19 wherein the plurality of pulleys are coupled together with a common cable, the cable and pulleys being coupled to move in unison circumferentially so as to move the plurality of dies radially inwardly.

21. Balloon pleating mechanism comprising:
- a plurality of pleating dies each including a first planar guiding surface, a second planar guiding surface, a bearing surface, a first working surface, and a second working surface;
- the plurality of pleating dies being arranged in a generally circular orientation with the first planar guiding surface of each die being in sliding contact with the second planar guiding surface of an adjacent die and the first working surface and the second working surface of each die cooperating to define a central cavity, the plurality of pleating dies being further arranged for relative radial movement between an open position and a closed position;
- a plurality of bearing structures, one each positioned between the first planar guiding surface of each die and the second planar guiding surface of an adjacent die;
- a plurality of bearing apparatus positioned to suspend each die and to hold the plurality of dies together in close sliding contact, one pair of bearing apparatus of the plurality of bearing apparatus being associated one each with each die of the plurality of dies, each bearing apparatus including a roller bearing positioned in engagement with the bearing surface of the associated die of the plurality of dies, the roller bearing of each bearing apparatus being mounted on a post having a fixed position with relation to the plurality of dies, and each of the posts is flexible and positioned to provide a radially inwardly directed bias on the plurality of dies; and
- a driving mechanism coupled to each die of the plurality of dies and designed to move the plurality of dies between the open position and the closed position, the driving mechanism including a plurality of pulleys, one pulley of the plurality of pulleys affixed one each to one die of the plurality of dies, the plurality of pulleys being coupled together with a common cable, the cable and pulleys being coupled to move in unison circumferentially so as to move the plurality of dies radially inwardly.

* * * * *